United States Patent [19]

Ackley et al.

[11] Patent Number: 5,719,033
[45] Date of Patent: Feb. 17, 1998

[54] THIN FILM TRANSISTOR BIO/CHEMICAL SENSOR

[75] Inventors: Donald E. Ackley, Lambertville, N.J.; Chan-Long Shieh, Paradise Valley, Ariz.

[73] Assignee: Motorola, Inc., Schaumburg, Ill.

[21] Appl. No.: 496,269

[22] Filed: Jun. 28, 1995

[51] Int. Cl.$^6$ ............... G01N 33/53; G01N 33/537; G01N 33/543
[52] U.S. Cl. ............... 435/7.92; 435/7.32; 435/7.95; 435/285.2; 436/524; 436/525; 436/527; 436/806; 422/82.01; 422/82.02; 422/82.11; 422/98; 204/400; 204/402; 204/403; 204/422
[58] Field of Search ............... 204/400, 402, 204/403, 422, 298.01; 422/82.01, 82.02, 82.03, 82.09, 82.11, 98; 435/7.32, 7.95, 285.2, 287.9, 288.7; 436/524, 525, 527, 806

[56] References Cited

U.S. PATENT DOCUMENTS

| | | |
|---|---|---|
| 4,238,757 | 12/1980 | Schenck . |
| 4,437,969 | 3/1984 | Covington et al. . |
| 4,709,987 | 12/1987 | Blackburn et al. . |
| 4,728,591 | 3/1988 | Clark et al. . |
| 4,877,582 | 10/1989 | Oda et al. . |
| 4,891,319 | 1/1990 | Roser . |
| 5,009,766 | 4/1991 | Lauks . |
| 5,165,005 | 11/1992 | Klainer et al. . |
| 5,234,566 | 8/1993 | Osman et al. . |
| 5,331,658 | 7/1994 | Shieh et al. . |
| 5,380,490 | 1/1995 | Hoshi et al. . |
| 5,403,772 | 4/1995 | Zhang et al. . |
| 5,481,527 | 1/1996 | Kasanuki et al. . |
| 5,489,988 | 2/1996 | Ackley et al. . |
| 5,500,188 | 3/1996 | Hafeman et al. . |
| 5,563,426 | 10/1996 | Zhang et al. . |
| 5,563,900 | 10/1996 | Ackley et al. . |
| 5,567,301 | 10/1996 | Stetter et al. . |

*Primary Examiner*—Christopher L. Chin
*Assistant Examiner*—Bao-Thuy L. Nguyen
*Attorney, Agent, or Firm*—Eugene A. Parsons

[57] ABSTRACT

A chemical sensor includes a thin film transistor with a gate positioned on one side. An insulating layer is positioned on the opposite side and an indicator film is positioned on the insulating layer in generally opposed relationship to the gate. Induced charge in the indicator film caused by a biological or chemical species changes the channel current in the transistor. A potential on the gate is then used to null out the resulting change in channel current. The potential used to null out the current change is an extremely sensitive measure of the induced charge.

11 Claims, 1 Drawing Sheet

THIN FILM TRANSISTOR BIO/CHEMICAL SENSOR

FIELD OF THE INVENTION

The present invention pertains to sensors and more specifically to bio/chemical sensors.

BACKGROUND OF THE INVENTION

Sensors and especially sensors capable of sensing biological and/or chemical species are coming into great demand. At the present time, sensors capable of performing these functions are relatively difficult to manufacture and are, consequently, relatively expensive.

Most of the known sensors utilize a material with a changing characteristic, such as resistance. The sensor then must be incorporated into an electronic circuit capable of utilizing (sensing) the changing characteristic. For example, a film of material can be incorporated into a Wheatstone bridge type of apparatus to sense a change in the resistance caused by a chemical, either in liquid, or gaseous form. The problem is that some form of amplification is generally required to bring the sensitivity of the sensor into a practical, or useful, range.

Thus, it would be highly advantageous to provide an extremely sensitive sensor which is relatively inexpensive to manufacture.

Accordingly, it is a purpose of the present invention to provide a new and improved bio/chemical sensor.

It is another purpose of the present invention to provide a new and improved bio/chemical sensor which is relatively inexpensive to manufacture.

It is still another purpose of the present invention to provide a new and improved bio/chemical sensor which is extremely sensitive.

It is still another purpose of the present invention to provide a new and improved bio/chemical sensor with enhanced reliability and with significantly relaxed packaging restraints.

It is yet another purpose of the present invention to provide a new and improved bio/chemical sensor which can easily be purged of the biological or chemical species being sensed.

It is a further purpose of the present invention to provide a new and improved sensor which can easily be adapted to sense a large variety of biological and chemical species, light, or movement.

It is a still further purpose of the present invention to provide a new and improved sensor in which various compensating techniques can easily be incorporated to allow for natural changes in the sensor.

SUMMARY OF THE INVENTION

The above problems are at least partially solved and the above purposes are realized in a chemical sensor including a thin film transistor with a gate positioned on one side and an indicator film positioned on an insulated layer on the opposite side in generally opposed relationship to the gate. Induced charge, or charge displacement, in the indicator film caused by a biological or chemical species changes the channel current in the transistor. A potential on the gate is then used to null out the resulting change in channel current. The potential used to null out the current change is an extremely sensitive measure of the induced charge.

In another embodiment the indicator film is a photosensitive film in which light induces or displaces a charge. Also, by using the biological material bacteriorhodopsin, which has a differential response to optical signals, for the indicator film, a motion sensor is provided.

BRIEF DESCRIPTION OF THE DRAWINGS

Referring to the drawings.

DESCRIPTION OF THE PREFERRED EMBODIMENTS

Figure 1:
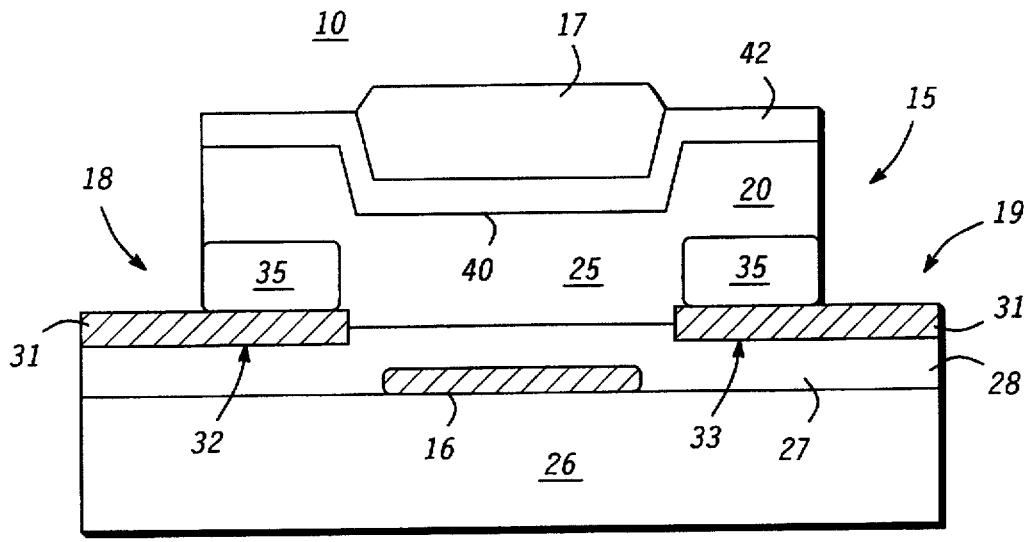
FIG. 1 is a simplified sectional view of an embodiment of a bio/chemical sensor in accordance with the present invention.

Turning now to the figures, FIG. 1 is a simplified sectional view of an embodiment of a bio/chemical sensor 10 in accordance with the present invention. Sensor 10 includes a thin film transistor 15 with an insulated gate 16 positioned on one side thereof. An indicator film 17 is positioned on an opposite side of transistor 15, generally in opposed relationship to gate 16. A source terminal 18 and a drain terminal 19 are formed, as a part of transistor 15, on opposite sides of gate 16, and a semiconducting layer 20 forms a current channel 25 therebetween. Also, gate 16 and indicator film 17 are positioned on opposite sides of semiconducting layer 20.

In the embodiment illustrated in FIG. 1, a supporting substrate 26 is provided and a layer of conductive material is patterned on a surface 27 of supporting substrate 26 to define gate 16. Supporting substrate 26 may be any convenient material and in the present embodiment is a plate of glass. It should be understood that gate 16 will generally have an external connection thereto for purposes to be described presently, which external connection is not shown in FIG. 1 for convenience. This external connection can be formed at the same time that gate 16 is patterned and will generally extend to an accessible area of supporting substrate 26.

An insulating layer 28 is deposited over gate 16, which may be any convenient material, such as silicon nitride (SiNx) or the like. An electrically conductive material 31 is deposited in two spaced apart areas 32 and 33 on insulating layer 28. Spaced apart areas 32 and 33 are spaced laterally from and on opposite sides of gate 16 and define the positions for source terminal 18 and drain terminal 19. Semiconductor material 35 is deposited on electrically conductive material 31 in areas 32 and 33 and semiconducting layer 20 is deposited over semiconductor material 35 and insulating layer 28 to form current channel 25. Conductive material 31 and semiconductive material 35 are selected to form an ohmic contact with semiconducting layer 20 at each of source terminal 18 and drain terminal 19.

Generally, thin film transistor 15 may be formed from any of the many well known material systems, such as hydrogenated amorphous silicon (a-Si:H), amorphous silicon (a-Si), poly-silicon, cadmium selenide (CaSe), organic semiconductors, or the like. In a specific example, semiconducting layer 20 is formed of hydrogenated amorphous silicon and semiconductive material 35 is formed of hydrogenated amorphous silicon which is doped to provide good N+ type conduction. Insulating layer 28 is formed of any compatible material, in this specific example silicon nitride (SiNx). Conductive material 31 and gate 16 may be any convenient metal or other convenient conductive material.

Semiconducting layer 20 has defined thereon an overlying surface 40 which generally overlies gate 16. Surface 40 is illustrated as a slightly depressed area in the upper surface of semiconducting layer 20, but it should be understood that the upper surface may be planar in some specific embodiments. Generally, the distance between surface 40 and insulating layer 28 is selected to provide proper operation of transistor 15, as will be understood by those skilled in the art. In instances where semiconducting layer 20 is conformally deposited, the distance between surface 40 and insulating layer 28 is determined by the thickness of semiconducting layer 20 and the upper surface appears generally as illustrated in FIG. 1.

An insulating layer 42 is deposited on the upper surface of semiconducting layer 20 and especially on surface 40. Insulating layer 42 may be a layer of silicon dioxide grown on the surface of semiconducting layer 20, or it may be formed of the same material as insulating layer 28, or any other convenient insulating material. In this disclosure, the term "deposited" is assumed to include any of the well known methods of providing a layer of material on another layer of material. Indicator film 17 is then deposited on surface 40 of insulating layer 42. Indicator film 17 may be, for example, a bio/chemical material, e.g. organometallic complexes such as rhodium-based material or various antibody layers that are extremely sensitive to biological species. Also, in other configurations, indicator film 17 may be a photosensitive layer including organic or inorganic photodiode material. Further, by using halobacteria bacteriorhodopsin, which has a time derivative response to optical signals, a motion detector may be readily produced.

In some applications of sensor 10, a material or species to be sensed becomes attached to indicator film 17 by absorption, electrical attraction, chemical bonding or other phenomenon (depending upon film 17 and the material being sensed), which induces an electrical charge or charge displacement in indicator film 17. In the event that sensor 10 is being used as a phototransistor, indicator film 17 is sensitive to the occurrence of light impinging thereon, which induces an electrical charge therein. Because indicator film 17 is positioned in juxtaposition to channel 25, it operates similar to a gate or control terminal for transistor 15. Thus, the induced charge or charge displacement in indicator film 17 causes a change in electrical current through channel 25. A potential on gate 16 is then applied to null the change in electrical current through channel 25. The potential on gate 16 can be calibrated or otherwise used as an extremely sensitive indicator or measure of the material, species or occurrence being sensed.

In addition to using gate 17 in the measuring or indicating process, gate 17 also allows the stabilization of a baseline for sensor 10. Generally, thin film transistors are susceptible to threshold voltage shifts (these can be on the order of 1 to 2 volts in "good" devices) which produce shifts in the baseline. Sensor 10 is easily adaptable to overcome these baseline shifts in several ways. For example, indicator film 17 can be periodically exposed to a "clean environment" and the potential on gate 16 can be adjusted to zero out any channel current. In another example, a differential pair of sensors 10 are provided, with indicator film 17 of one of the sensors being passivated. Since the baseline drift in both sensors 10 will be nearly the same, the signal from the reference sensor 10 (passivated indicator film 17) may be utilized to compensate for any changes in the other sensor 10.

In some applications (generally depending upon material being sensed and indicator film 17), sensor 10 can be purged or renewed by applying a relatively large potential to gate 16. The large potential should be the same charge as any net charge on the material being sensed and will generally be large relative to the net charge so as to repel the sensed material from indicator film 17. For example, if positive ions are being sensed, the net charge is the charge on each ion. This novel method of purging or renewing sensor 10 is a substantial advantage since it can be performed with sensor 10 in position and no additional labor is required.

Figure 2:
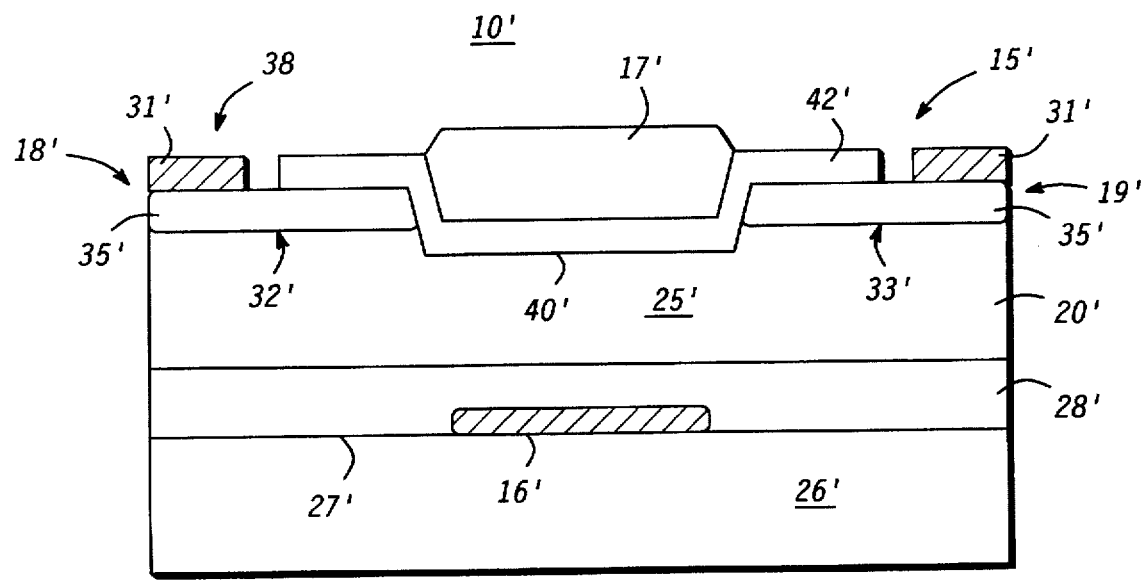
FIG. 2 is a simplified sectional view of another embodiment of a bio/chemical sensor in accordance with the present invention.

Turning now to FIG. 2, a simplified sectional view of an embodiment of a bio/chemical sensor 10' in accordance with the present invention is illustrated. In this embodiment, similar components are designated with similar numbers and all of the numbers have a prime added to indicate a different embodiment. Sensor 10' includes a thin film transistor 15' with a gate 16' positioned on one side thereof. An insulated indicator film 17' is positioned on an opposite side of transistor 15', generally in opposed relationship to gate 16'. A source terminal 18' and a drain terminal 19' are formed, as a part of transistor 15', on opposite sides of gate 16', and a semiconducting layer 20' forms a current channel 25' therebetween. Also, gate 16' and indicator film 17' are positioned on opposite sides of semiconducting layer 20'.

In the embodiment illustrated in FIG. 2, a supporting substrate 26' is provided and a layer of conductive material is patterned on a surface 27' of supporting substrate 26' to define gate 16'. Supporting substrate 26' may be any convenient material and in the present embodiment is a plate of glass. As previously explained, gate 16' will generally have an external connection thereto, which external connection is not shown in FIG. 2 for convenience. This external connection can be formed at the same time that gate 16' is patterned and will generally extend to an accessible area of supporting substrate 26'.

An insulating layer 28', which may be any convenient material, such as silicon nitride (SiNx) or the like, is deposited on supporting substrate 26' and over gate 16'. Semiconducting layer 20' is deposited on insulating layer 28' and semiconductor material 35' is deposited on the surface of semiconducting layer 20' in spaced apart areas 32' and 33'. Spaced apart areas 32' and 33' are spaced laterally from and on opposite sides of gate 16' and define the positions for source terminal 18' and drain terminal 19'. Also, in this embodiment, semiconductor material 35' (and, in some applications, a portion of semiconducting layer 20') is removed by chemical etching, or other means well known in the art, in a region positioned in generally opposed relationship to gate 16'. In the embodiment of FIG. 2, an overlying surface 40' is defined by the etching in semiconductor layer 20'.

Metal or other good conducting material 31' is deposited on the surface of semiconductor material 35' in areas 32' and 33' to form electrical contacts for source terminal 18' and drain terminal 19', respectively. An insulating layer 42' is deposited on surface 40' of semiconducting layer 20' and on semiconductor material 35' to insulate indicator layer 17' from source terminal 18' and drain terminal 19'. Indicator film 17' is then deposited on insulating layer 42' in overlying relationship to surface 40', so as to be in generally opposed relationship to gate terminal 16'.

As described above, indicator film 17' is introduced to a material, species, or occurrence to be sensed, which material, species, or occurrence induces an electrical charge or charge displacement in indicator film 17'.

Because indicator film 17' is positioned in juxtaposition to channel 25', it operates similar to a gate or control terminal for transistor 15'. Thus, the induced charge or charge displacement in indicator film 17' causes a change in electrical current through channel 25'. A potential on gate 16' is then applied to null the change in electrical current through channel 25'. The potential on gate 16' is calibrated or otherwise used as an extremely sensitive indicator or measure of the material, species or occurrence being sensed.

Thus, bio/chemical sensors have been disclosed which are relatively inexpensive to manufacture, are scaleable to large sensor arrays, and are extremely sensitive. Further, the new and improved bio/chemical sensors can easily be purged of the biological or chemical species being sensed and can easily be adapted to sense a large variety of biological and chemical species, light, or movement (occurrences). Also, various compensating techniques can easily be incorporated in the new and improved sensors to allow for natural changes in the sensors. The new and improved bio/chemical sensors provide enhanced reliability and manufacturability with significantly relaxed packaging restraints. One example where an improvement in packaging is realized occurs when all electrical contacts are placed below the semiconducting layer (e.g. layer 20). The contacts may then be addressed through vias in the supporting substrate. In this configuration the only surface exposed to the ambient (hostile) environment is the indicator film, which results in enhanced reliability and significantly eases packaging restraints.

While we have shown and described specific embodiments of the present invention, further modifications and improvements will occur to those skilled in the art. We desire it to be understood, therefore, that this invention is not limited to the particular forms shown and we intend in the appended claims to cover all modifications that do not depart from the spirit and scope of this invention.

What is claimed is:

1. A chemical sensor comprising:

a thin-film transistor including a semiconducting layer, source and drain terminals engaged with the semiconducting layer in spaced apart relationship to define a current channel in the semiconducting layer, and a gate terminal engaged with a first side of the semiconducting layer in juxtaposition to the current channel so as to control current flow between the source and drain terminals through the current channel when the source, drain and gate terminals are activated; and an indicator film sensitive to a material or species, the indicator film being positioned adjacent to a second side of the semiconducting layer in juxtaposition to the current channel, the indicator film changing current flow between the source and drain terminals through the current channel, when the source and drain terminals are activated, in response to the material or species being sensed by the indicator film;

wherein, the gate terminal is separated from the indicator film by the current channel.

2. A chemical sensor as claimed in claim 1 wherein each of the source and drain terminals include a doped layer of semiconducting material positioned on a surface of the semiconducting layer and an electrical contact positioned on the doped layer of semiconducting material.

3. A chemical sensor as claimed in claim 1 wherein the gate terminal includes an insulating layer of material positioned on a surface of the semiconducting layer and an electrical contact positioned on the insulating layer of material.

4. A chemical sensor as claimed in claim 1 wherein the semiconducting layer includes one of amorphous silicon, hydrogenated amorphous silicon, poly-silicon, cadmium selenide, or organic semiconductor.

5. A chemical sensor as claimed in claim 1 wherein the indicator film includes an organometallic complex.

6. A chemical sensor as claimed in claim 5 wherein the organometallic complex includes a rhodium-based material.

7. A chemical sensor as claimed in claim 1 wherein the indicator film includes an antibody layer that is sensitive to biological species.

8. A chemical sensor as claimed in claim 1 wherein the indicator film includes a photodiode.

9. A chemical sensor as claimed in claim 8 wherein the photodiode includes an organic photodiode.

10. A chemical sensor as claimed in claim 1 wherein the indicator film includes a photosensitive film.

11. A chemical sensor as claimed in claim 10 wherein the photosensitive layer includes halobacteria bacteriorhodopsin.

* * * * *